United States Patent [19]

Ozawa

[11] Patent Number: 5,178,152
[45] Date of Patent: Jan. 12, 1993

[54] ELECTRONIC SPHYGMOMANOMETER

[75] Inventor: Hitoshi Ozawa, Fujinomiya, Japan

[73] Assignee: Terumo Corporation, Tokyo, Japan

[21] Appl. No.: 403,001

[22] Filed: Sep. 6, 1989

Related U.S. Application Data

[63] Continuation of Ser. No. 330,957, Mar. 29, 1989, abandoned, which is a continuation of Ser. No. 39,233, Apr. 17, 1987, abandoned.

[30] Foreign Application Priority Data

Apr. 21, 1986 [JP] Japan .................................. 61-90080
Apr. 21, 1986 [JP] Japan .................................. 61-90081

[51] Int. Cl.$^5$ .............................................. A61B 5/04
[52] U.S. Cl. ................................................... 128/680
[58] Field of Search ................. 128/672, 677, 680-682

[56] References Cited

U.S. PATENT DOCUMENTS

| | | | |
|---|---|---|---|
| 4,206,765 | 6/1980 | Huber | 128/677 |
| 4,290,434 | 9/1981 | Jewett . | |
| 4,301,512 | 11/1981 | Keith et al. | 128/668 |
| 4,312,359 | 1/1982 | Olson . | |
| 4,331,154 | 5/1982 | Broadwater et al. | 128/690 |
| 4,479,494 | 10/1984 | McEwen . | |
| 4,493,326 | 1/1985 | Hill et al. | 128/680 |
| 4,519,398 | 5/1985 | Lisiechi et al. | 128/710 |
| 4,531,527 | 7/1985 | Reinhold, Jr. et al. | 128/696 |
| 4,610,254 | 9/1986 | Morgan et al. | 128/419 D |
| 4,625,277 | 11/1986 | Pearce et al. | 128/681 |
| 4,627,440 | 12/1986 | Ramsey, III et al. | 128/685 |

FOREIGN PATENT DOCUMENTS

| | | | |
|---|---|---|---|
| 616801G | 4/1980 | France . | |
| 2168487 | 6/1986 | United Kingdom | 128/682 |

OTHER PUBLICATIONS

Weihs, J. A., European Search Report, Berlin.

Primary Examiner—David M. Shay
Attorney, Agent, or Firm—Staas & Halsey

[57] ABSTRACT

An electronic sphygmomanometer includes CPU-controlled peripheral elements such as a pump, an amplifier, an A/D converter and a printer. During measurement of blood pressure, power consumption is reduced by supplying power to these peripheral elements only when they are driven or operated. When a blood pressure measurement or a print-out of measured values ends, the CPU acts to cut off its own power to reduce power consumption further. The sphygmomanometer further includes a timer constantly supplied with power for the purpose of preserving time information. Operating power is supplied to the CPU in synchronism with a pulse signal outputted by the timer every minute. When the pulse signal arrives, the CPU reads in time information from the timer, causes the time information to be displayed by a display device, then cuts off its own power and waits for the next pulse signal. By repeating such processing, time is displayed while power consumption is minimized.

12 Claims, 4 Drawing Sheets

ELECTRONIC SPHYGMOMANOMETER

This application is a continuation of prior complete application Ser. No. 07/330,957, filed on Mar. 29, 1989, now abandoned, which is a continuation of prior complete application Ser. No. 07/039,233, filed on Apr. 17, 1987, now abandoned.

BACKGROUND OF THE INVENTION

This invention relates to an electronic sphygmomanometer and, more particularly, to an electronic sphygmomanometer in which power consumed due to activation of a plurality of independent circuits and peripheral devices is reduced.

In a conventional electronic sphygmomanometer, measurement processing is performed following introduction of electric power to various independent circuits and peripheral devices by a manual operation. The manual introduction of power to the peripheral devices is a troublesome operation. Moreover, during measurement or the printing out of results, the particular processing is executed while power remains applied to devices or circuits which are not participating. Power consumption is high as a result.

In particular, an electronic sphygmomanometer having a timekeeping function is adapted to display date and time information when blood pressure is measured. Since the time, for example, is displayed in a display window constantly regardless of whether the window cover is open or closed, the amount of power consumed by the display is significant. Though it has been contemplated to display the time information in the display window only when the cover is open, power continues to be supplied to the control unit (namely a CPU and its peripheral circuitry) during the time that a switch or the like for starting blood pressure measurement is in the ON state. For this reason, the reduction in power consumption is still inadequate.

SUMMARY OF THE INVENTION

Accordingly, an object of the invention is to provide an electronic sphygmomanometer in which power consumption is curtailed by executing blood pressure processing upon introducing power only to peripheral elements required at the time of such processing.

Another object of the invention is to provide an electronic sphygmomanometer in which power can be supplied to peripherals automatically to simplify and facilitate operation.

According to the present invention, the foregoing objects are attained by providing an electronic sphygmomanometer which comprises a plurality of peripheral elements related to blood pressure measurement, processing means for executing blood pressure measurement by controlling the peripheral elements, and switching means connected to the processing means for enabling power to be supplied to the peripheral elements only for a time required when processing is executing by the processing means. In accordance with this arrangement, power consumption is reduced by executing processing upon introducing power only to peripheral elements required at the time of blood pressure measurement. In addition, the supply of power to the peripherals is automated to make the sphygmomanometer easy to use.

In an embodiment of the invention, the electronic sphygmomanometer is further provided with a memory for storing plural items of blood pressure information whenever a measurement is performed, the memory being supplied with power at all times to preserve this blood pressure information. Data indicative of measured values therefore will not be erased. In another embodiment of the invention, the electronic sphygmomanometer, one of the peripheral elements is a printer for printing out blood pressure information. This enables a reduction in power consumed when the printer is used. The period of time during which power is supplied to the printer ends when the printing operation is completed. Thus, power consumption can be curtailed by not supplying power to the printer needlessly. The electronic sphygmomanometer may further include a manual switch for supplying power to the processing means in order to command print-out of the measured blood pressure information, the processing means responding to actuation of the manual switch by supplying driving power to the printer during completion of a printing output in order to print out the blood pressure information.

In still another embodiment, one of the peripheral elements is a pump for admitting air pressure to the interior of a cuff used in blood pressure measurement. Thus, power consumption can be reduced by applying power to the pump only when necessary. The period of time during which power is supplied to the pump ends when pressure inside the cuff attains a predetermined pressure value. Thus, power consumption can be curtailed by not supplying power to the pump needlessly. The electronic sphygmomanometer may further include a manual switch for supplying power to the processing means in order to instruct the start of blood pressure measurement. When the manual switch is actuated, the processing means supplies driving power to the pump until the pressure inside the cuff attains the predetermined pressure value in order to start blood pressure measurement. Power consumption can thus be reduced by supplying power only when the pump is used.

Further, according to the invention, the peripheral elements include an amplifier for amplifying an analog signal from a pressure sensor for sensing pressure inside a pressure cuff, and an analog Korotkoff signal from a microphone inside the pressure cuff, and an A/D converter for converting the analog signals amplified by the amplifier into digital signals. Power consumption can be reduced by supplying power to the amplifier and A/D converter only when they are used.

In an embodiment, the period of time during which power is supplied to the amplifier and A/D converter is that during which a blood pressure measurement is performed. Thus, power consumption can be curtailed by not supplying power to the amplifier and A/D converter needlessly.

In yet another embodiment, a source of power is a battery power supply incorporated in the electronic sphygmomanometer. This enables the service life of the battery to be extended.

In another embodiment, the source of power is a commercial power supply external to the electronic sphygmomanometer. This enables power consumption to be reduced.

Still another object of the present invention is to provide an electronic sphygmomanometer in which the amount of power consumption is reduced by cutting off power supplied to processing means per se when the processing means completes the execution of processing by controlling a peripheral element.

According to the invention, this object is attained by providing an electronic sphygmomanometer which comprises a peripheral element used in blood pressure measurement, processing means for executing blood pressure measurement by controlling the peripheral element, commanding means connected to the processing means for commanding the start of processing related to blood pressure measurement, and power supply means for supplying power to the processing means in response to a command from the commanding means. The processing means has detecting means for detecting the end of processing commanded by the commanding means, and deactivating means for deactivating the power supply means in response to detection of the end of processing by the detecting means. Thus, the amount of power consumption is reduced by cutting off power supplied to the processing means itself when the processing means completes the execution of processing by controlling the peripheral element.

According to an embodiment of the invention, the peripheral element is a printer for printing out information relating to blood pressure values, and the commanding means is a manual switch for commanding print out. This arrangement makes it possible to reduce further the consumption of power prior to the print-out.

In another embodiment, the peripheral element is a printer for printing out information relating to blood pressure values, and the detecting means detects that the processing means has outputted to the printer all information that is to be printed.

In another embodiment, the peripheral element is a pump for feeding air pressure into a cuff used in blood pressure measurement, and the commanding means is a manual switch for driving the pump prior to the start of blood pressure measurement. This arrangement makes it possible to reduce further the consumption of power prior to blood pressure measurement.

In a further embodiment, the peripheral element is a pump for feeding air pressure into a cuff used in blood pressure measurement, and the detecting means detects that blood pressure measurement has ended when pressure inside the cuff attains a predetermined pressure value. Thus, power consumption can be reduced since power is supplied to the processing means only during blood pressure measurement.

Yet another object of the invention is to provide an electronic sphygmomanometer in which power consumed for the purpose of a time display is minimized.

According to the invention, this object is attained by providing an electronic sphygmomanometer which comprises: an electronic sphygmomanometer body having timekeeping means supplied with power at all times for outputting a pulse signal of a predetermined duration at a fixed period and for holding time information, processing means for executing blood pressure measurement, and display means for displaying information relating to measured blood pressure values; and cover means for covering at least the display means; the electronic sphygmomanometer body further including first power supply means for supplying the display means with power in response to detecting that the cover means is open, and second power supply means for supplying power to the processing means, on the basis of the signal outputted by the timekeeping means, when the display means is placed in a display enable state by the first power supply means; the processing means including read-in means for reading in time information from the timekeeping means when power is supplied by the second power supply means; output means for outputting the time information to the display means; and deactivating means for deactivating the second power supply means after the display means displays the time information outputted by the output means. This arrangement makes it possible to minimize power consumed by the time display.

In an embodiment of the invention, the cover means is a cap covering the upper face of the electronic sphygmomanometer body. Power consumed by the time display can be minimized even when the cap is open, and the cap makes it possible to protect at least the upper face of the electronic sphygmomanometer body.

In another embodiment, the cover means is a case for accommodating the electronic sphygmomanometer body. Thus, power consumed by the time display can be minimized and the case makes it possible to protect the electronic sphygmomanometer.

In a further embodiment, the period of the pulse signal outputted by the timekeeping means is one minute. This makes it possible to update the least significant digit of the time display.

In still another embodiment, the width of the pulse signal outputted by the timekeeping means corresponds to at least a period of time from the leading edge of the pulse signal until the processing means becomes operational. This assures that the processing means will operate in a reliable manner.

In yet another embodiment, the electronic sphygmomanometer further includes a memory for storing plural items of blood pressure information whenever a measurement is performed, the memory being supplied with power at all times to hold this blood pressure information. Data indicative of measured values therefore will not be erased.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 3(a) is a sectional view of the electronic sphygmomanometer embodying the present invention; and FIGS. 3(b) and (c) are views illustrating the relationship between a cover and a switch.

DESCRIPTION OF THE PREFERRED EMBODIMENT

An embodiment of the present invention will now be descrbed in detail with reference to the accompanying drawings.

In the following embodiment, the electronic sphygmomanometer is powered by a battery, by way of example.

Figure 1:
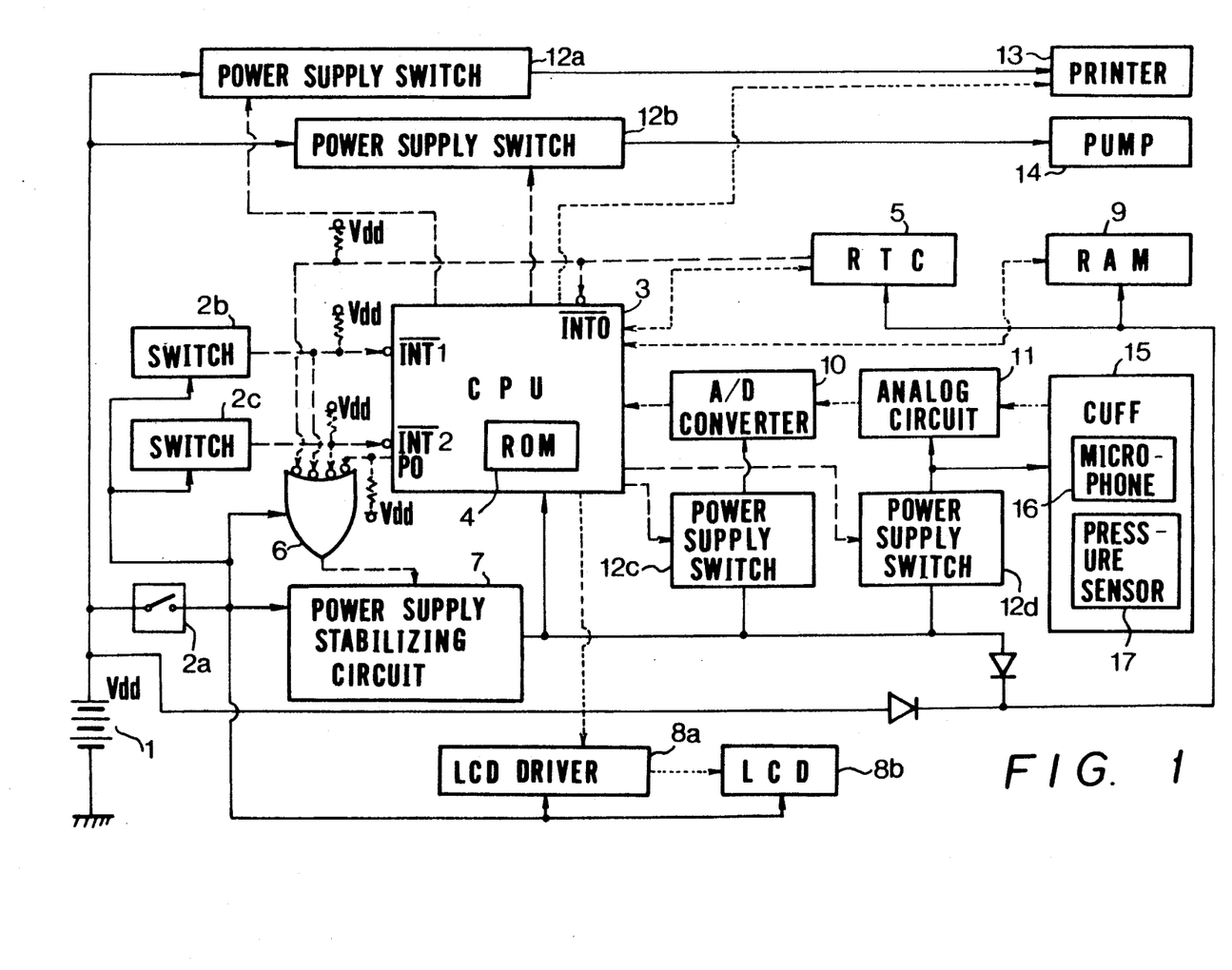
FIG. 1 is a block diagram of an electronic sphygmomanometer embodying the present invention.

In the block diagram of FIG. 1, the solid lines indicate power supply lines, the dashed lines represent control lines between a CPU 3 and a switch 2a, described below, and the dotted lines represent data exchange lines, primarily a data bus. The circuits and peripheral devices of the overall block diagram are supplied with electric power by a battery 1. The battery 1 is connected to the switch 2a which discriminates whether, e.g., a cover of the the electronic sphygmomanometer is in place. If the cover has been removed from the electronic sphygmomanometer, the switch 2a closes to provide a power supply stabilizing circuit 7, switches 2b, 2c, and LCD drivers 8a, 8b, described below, with power from the battery 1.

Figure 3:
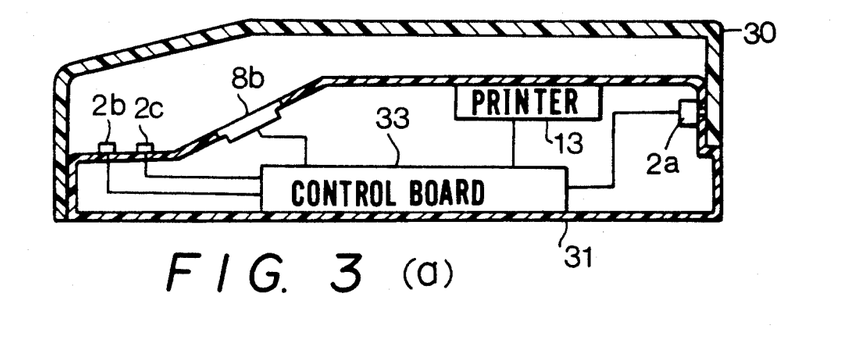

As shown in (a) of FIG. 3, the switch 2a is situated at e.g. the rear of the electronic sphygmomanometer body, designated by numeral 31. Disposed within the electronic sphygmomanometer body is a control board 33 comprising an IC, which includes the CPU 3, and various LSIs. The switch 2a has a head 2a' which, in the state shown in (b) of FIG. 3, is caused to recede to the left of the body 31 by a cover 30 acting upon a button 32 the base end of which is in abutting contact with the head 2a'. In this state the switch is off, i.e. open. FIG. 3(c) depicts the state which prevails when the cover 30 is removed from the body 31. Since removing the cover removes the leftward urging force from the button 32, the latter is thrust rightward beyond the face of the body 31 by the restoring force of the head 2a', whereby the switch 2a is turned on or closed. There is no particular limitation upon the configurations and positions of the cover 30 and switch 2a as long as the switch 2a is capable of discriminating whether the cover 30 is open or closed. It is permissible to connect the cover 30 to the electronic sphygmomanometer body by a hinge. It is also possible to place the entirety of the electronic sphygmomanometer body in a case, rather than provide the body with the cover 30. In other words, since it will suffice to adopt an arrangement in which it can be detected when the electronic sphygmomanometer is not in use, the easiest approach is to provide the cover 30 for covering at least the display, which is an LCD 8b. The cover 30 is useful in protecting at least the upper face of the electronic sphygmomanometer when it is carried, while the case is advantageous in that it protects the entirety of the electronic sphygmomanometer.

Figure 2A:
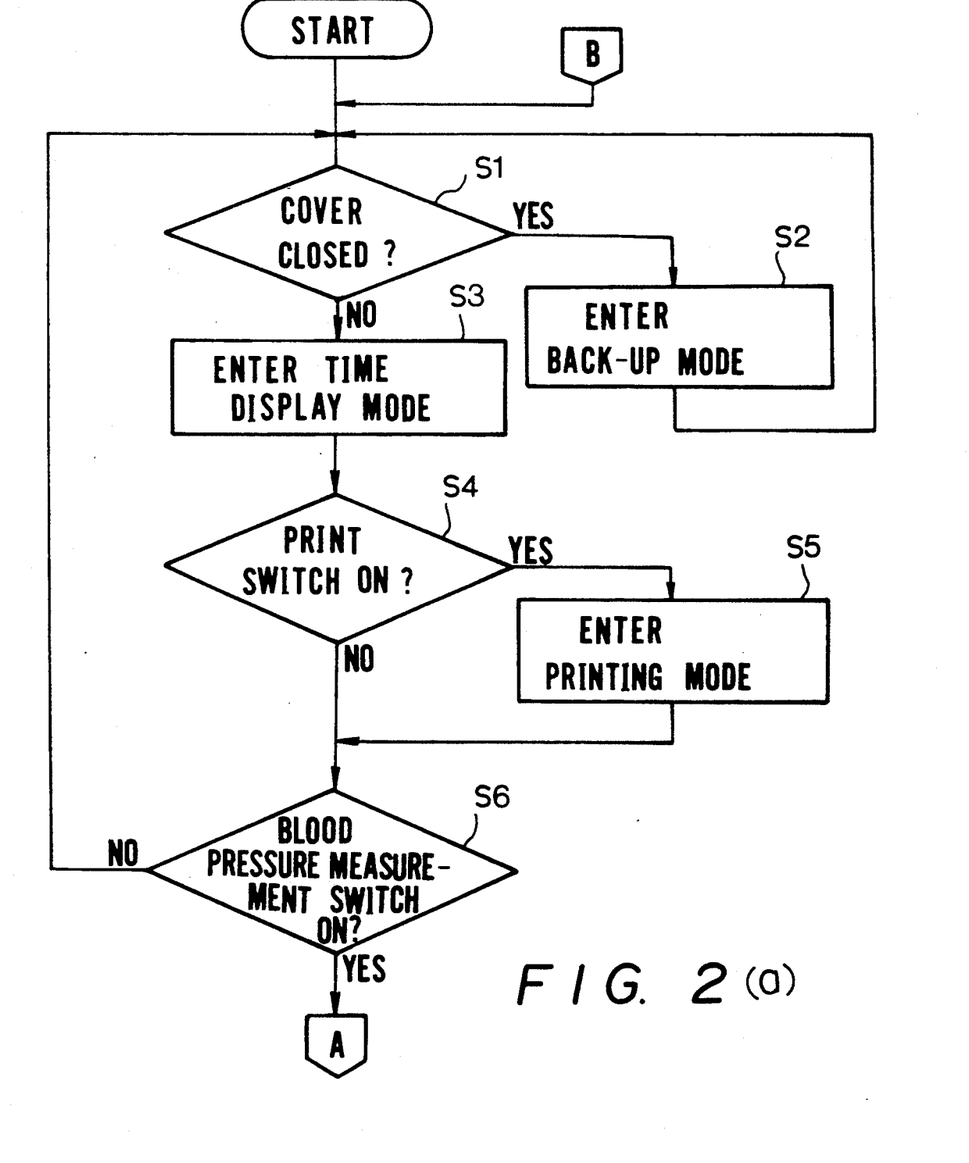
FIGS. 2(a) and (b) are flow charts illustrating operation of the electronic sphygmomanometer embodying the present invention.
Figure 2B:
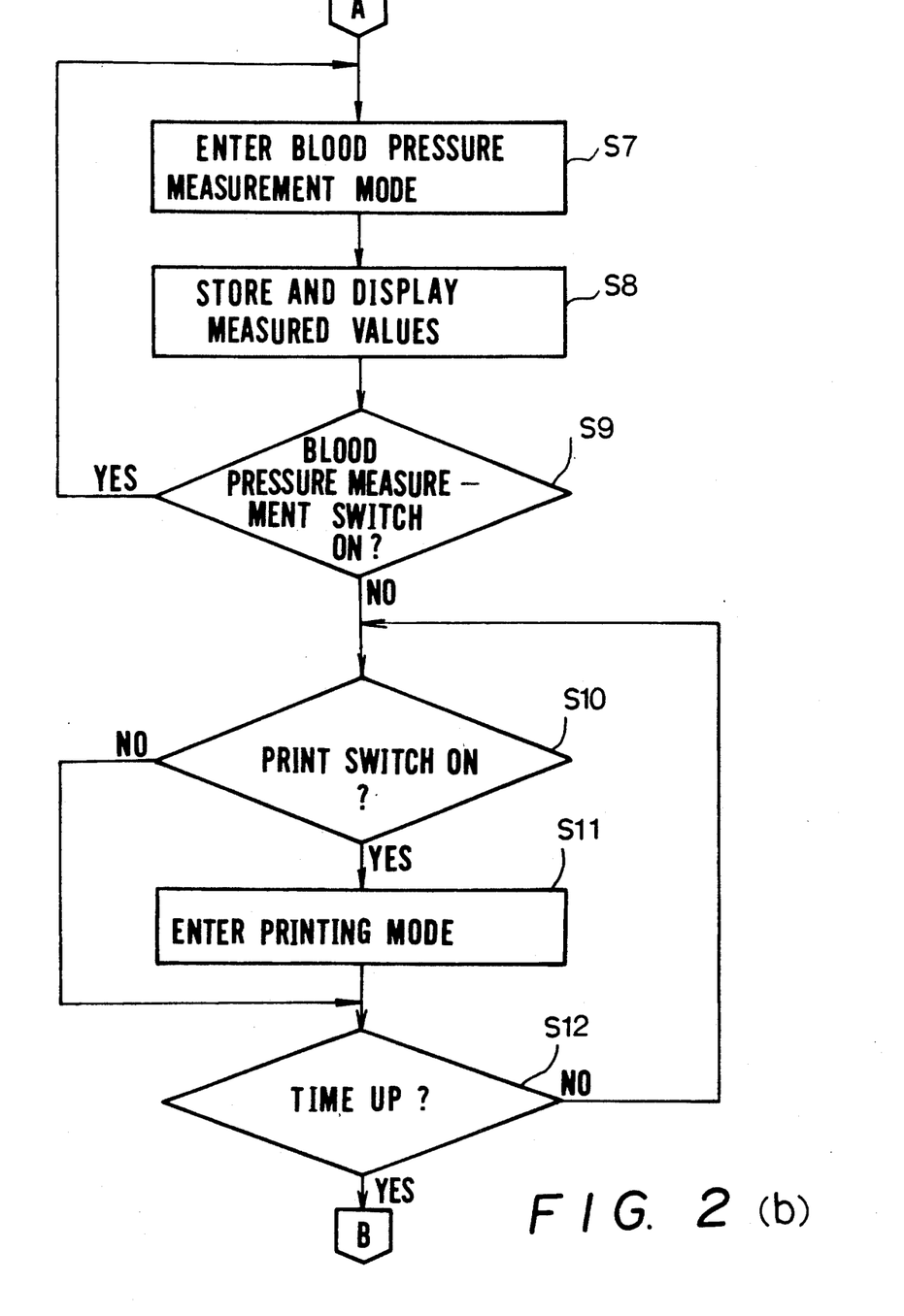

The switch 2b is for commanding the print-out of measured blood pressure values and information relating to the date and time of measurement. The switch 2c is for commanding the start of blood pressure measurement. The CPU 3 controls the various circuits and peripheral devices and includes a ROM 4 storing a control program illustrated by the flowchart of FIG. 2, described below. A real-time clock (hereinafter referred to as an "RTC") 5 is supplied with electrical power at all times and functions in the same manner as a clock, generating an interrupt signal every minute for application to the CPU 3. A gate 6 is actuated when the switch 2a closes. When at least one of the inputs thereto is logical "0", the gate 6 outputs logical "1". The output of gate 6 is applied to the power supply stabilizing circuit 7, which is for supplying stabilized power to various circuit and peripheral devices when the output of gate 6 is "1". Numeral 8 denotes an LCD driver which drives the LCD 8b for the display. The LCD driver 8a is supplied with power when the switch 2a is ON, namely when the cover 30 has been removed. A RAM 9 stores various data relating to measured values as well as information relating to the date and time of measurement. Like the RTC 5, the RAM 9 is supplied with power at all times for data back-up purposes. At the time of a blood pressure measurement, an A/D converter 10 receives an analog Korotkoff signal from a microphone 16 and an analog pressure level signal from a pressure sensor 17, which are provided in a pressure cuff 15, and converts these signals into digital signals applied to the CPU 3. An analog circuit 11 comprises an amplifier and the like for amplifying the Korotkoff signal and pressure level signal from the pressure cuff 15. Power supply switches 12a, 12b, 12c, 12d are controlled by the CPU 3 to control the supply of power to the a printer 13, pump 14, the A/D converter 10 and the analog circuit 11, respectively. Note that the control lines of the RTC 5 and switches 2b, 2c as well as an output terminal PO of the CPU 3 are pulled up to the logic level "Vdd" so as to attain a high level, namely logical "1", when the switch 2a is closed.

If the results of blood pressure measurement and the like are to be printed out at the end of measurement in the electronic sphygmomanometer having the foregoing construction, power need not be supplied to the pump 14. Conversely, when performing processing for printing or the like, it is unnecessary to drive or operate the analog circuit 11, the A/D converter 10 and a peripheral device such as the pump 14.

Thus, it will be appreciated that power should be supplied to each peripheral device and circuit as it is needed for a particular operation. The various processing stages and the circuits or peripheral devices required therefor are summarized generally in the following table. In the illustrated embodiment, the processing stages are described as being four in number, namely a back-up mode, time display mode, blood pressure measurement mode and printing mode, though these modes can be broken down further if desired. In the table, the symbol "x" under a mode means that the indicated device or circuit is not supplied with power when the mode of operation is executed. The symbol "Δ" means that the device or circuit is supplied with power sometimes when the particular mode of operation is executed. The symbol "○" indicates that the device or circuit is supplied with power at all times.

TABLE

|  | Back-Up Mode | Time Display Mode | Blood Pressure Meas. Mode | Printing Mode |
| --- | --- | --- | --- | --- |
| CPU | x | Δ | ○ | ○ |
| RTC & RAM | ○ | ○ | ○ | ○ |
| LCD & LCD Driver | x | ○ | ○ | ○ |
| Analog Circuit & A/D Converter | x | x | ○ | x |
| Power Supply Stabilizing Circuit | x | ○ | ○ | ○ |
| Pump | x | x | ○ | x |
| Printer | x | x | x | ○ |

Operation in each of these modes will now be described.

The back-up mode refers to the state in which the cover 30 is placed on the sphygmomanometer, namely in which power is being supplied to the RTC 5, serving as the clock, and to the back-up RAM 9. At this time, the RTC 5 provides the CPU 3 with an interrupt signal in the form of a negative signal having a predetermined duration. The signal is applied to the CPU 3 e.g. every minute, which is the least significant digit of the time display. This signal is also connected to the gate 6. Meanwhile, in order for the RAM 9 to hold data which is the result of previous measurement, the RAM is supplied with power at all times. In other words, the RAM is powered constantly for back-up purposes. In this mode, power is not supplied to the CPU 3, by way of example.

The time display mode refers to the state in which the cover 30 is removed from the electronic sphygmomanometer, on which occasion time is displayed by the LCD 8b, which constitutes the display means of the electronic sphygmomanometer. In this mode, the switch 2a is closed to supply power from battery 1 to the LCD 8b, LCD driver 8a, gate 6 and switches 2b, 2c. Since the output of gate 6 is logical "0" at this time, the power supply stabilizing circuit 7 does not output the supply voltage, so that the CPU 3 naturally remains without power. However, the RTC 5 is always operating, as the block diagram of FIG. 2 shows, and therefore is constantly providing the CPU 3 and the gate 6 every minute with the negative signal having the predetermined duration. In response to this signal applied thereto, the gate 6 outputs a logical "1" signal to the power supply stabilizing circuit 7, which is responsive to supply power to the CPU 3 and an IC, not shown, which is necessary for operating the CPU 3. When the CPU 3 receives power, the output PO thereof is immediately made "0" during the time that the output signal of the RTC 5 is at the "0" level. The "0" output PO prevents power from being cut off to the CPU 3 so that the latter may read in the current time from the RTC 5 and write the time data into the LCD driver 8a to latch the same. The driver 8a causes the LCD 8b to display the time data. When the above processing ends, the CPU 3 sends its output terminal PO to logical "1", whereby power to the CPU 3 per se is cut off. Note that even though power to the CPU 3 is cut off, the LCD driver 8a latches the time data so that the data continues to be displayed by the LCD 8b. Since the foregoing operation is performed every minute, in the time display mode the CPU 3 is supplied with power every minute rather than at all times, thus making it possible to reduce the power consumed by the CPU. For this reason, the CPU 3 is assigned the "Δ" mark in the "Time Display Mode" column of the table. In this mode, power need be supplied only to the RTC 5, RAM 9, LCD 8b, LCD driver 8a and the stabilizing circuit 7. Ordinarily, the arrangement is such that the CPU 3 is disabled immediately after the stabilizing circuit 7 supplies it with power. The reason is that a reset signal is supplied to the CPU 3 for several blocks so that the CPU 3 can execute the program reliably from the normal address. Accordingly, it is required that the pulse width of the pulse signal outputted by the RTC 5 be greater than this time interval at least.

In the blood pressure measurement mode, the output of the gate 6 goes to logical "1" in response to closure of the switch 2c, and power is supplied to the CPU 3, just as in the time display mode. The CPU 3 responds first by placing logical "0" at its output terminal PO to prevent power from being cut off to the CPU. The CPU 3 then applies signals to the power supply switches 12b–12d, as a result of which the switches are closed to supply power to the pump 14, A/D converter 10 and analog circuit 11, respectively. Thereafter, in accordance with a well-known processing procedure, pressure inside the cuff 15 is raised, a signal is received from the pressure sensor 17, operation of the pump 14 is halted when internal cuff pressure attains a predetermined level, air within the cuff 13 is discharged via a constant-rate discharge valve, not shown, thereby depressurizing the cuff, during which time pulse rate is measured, as well as systolic and diastolic blood pressure on the basis of Korotkoff sounds from the microphone 16. The results of blood pressure measurement, namely the systolic and diastolic blood pressure and pulse rate, are displayed on the LCD 8b by activating the LCD 8a. The results are also stored in the RAM 9. Next, the CPU 3 determines whether the switch 2b has been pressed for a prescribed period of time. If it has not, the CPU 3 removes signals from the power supply switches 12a–12d and then places logical "1" at its output terminal PO, whereby power is cut off from the CPU 3 and peripheral circuits. Strictly speaking, the period of time during which power is supplied to the pump 14 is not equal to the duration of blood pressure measurement. It will suffice if the power is supplied until cuff pressure reaches a predetermined value. In other words, the duration of power supplied to the pump 14 extends from the moment air begins to be fed into the cuff 15 until the predetermined value is attained.

The printing mode refers to outputting the previous item of measurement value data, which has been stored in RAM 9, or a currently measured blood pressure value and pulse rate to the printer 13. When the CPU 3 senses that the switch 2b has been pressed, it first places logical "0" at its output terminal PO to prevent a cut-off in power, just as in the blood pressure measurement mode. The CPU 3 then turns on the power supply switch 12a to introduce power to the printer 13. Thereafter, the data stored in RAM 9 are outputted to the printer 13. When printing is completed, the CPU 3 again raises its output PO to logical "1" to remove power from the CPU.

This completes the description of each mode of processing. The flow of a series of these processing steps will now be described with reference to the flowchart of FIGS. 2(a) and (b). Each mode mentioned in the flowchart is as set forth above.

Step S1 of the flowchart call for a determination as to whether the cover 30 of the electronic sphygmomanometer has been closed. If the answer is YES, then the sphygmomanometer operates in accordance with the back-up mode at S2. If the cover 30 has not been closed, on the other hand, the time display mode is established at step S3 in response to the signal by the RTC 5 every minute. This causes the LCD 8b to display the time. The program then proceeds to step S4, at which it is determined whether the print switch 2b is ON. If this switch is found to be ON, the program proceeds to a step S5, at which the printing mode is established and the CPU 3 reads in the previous measurement data from the RAM 9 and outputs it to the printer 13. Next, it is determined at step S6 whether the blood pressure measurement switch 2c is ON. If the answer is NO, the program returns to step S1. If the switch 2c is ON, then the program proceeds to step S7, at which the blood pressure measurement mode is established. Accordingly, systolic and diastolic blood pressure and pulse rate are measured, and the resulting data are displayed by the LCD 8b via the LCD driver 8a at step S8, and currently stored in the RAM 9 together with the data of time and date when the measurement has been performed at the same step. This is followed by step S9, at which the status of blood pressure measurement switch 2c is sensed. If the switch is ON, then processing is repeated from step S7 onward; if the switch is OFF, the status of the print switch 2b is sensed at step S10. When the switch 2b is found to be ON, the data resulting form the measurement performed at step S7 are outputted to the printer. When the switch 2b is OFF, on the other hand, the operation for sensing the status of switch 2b is repeated for a predetermined period of time. If the switch remains OFF longer than the predetermined time period, the program returns to step S1.

Thus, in accordance with the present embodiment as described above, power is supplied only to the circuits and peripheral devices required for each type of processing, thereby enabling a reduction in power consumption. When a battery is employed as the power source, the service life thereof can be prolonged.

By automating the delivery and removal of power to and from the peripheral devices, less labor is involved in operating the sphygmomanometer This arrangement also assures that power to the peripherals will not be left on inadvertently. Moreover, the fact that the measurement data are stored in the constantly powered RAM assured that the data will not be erased accidentally.

If the switch for starting blood pressure measurement or the switch for starting printing processing is not pressed again within a predetermined period of time after blood pressure measurement or measured value print-out processing, power is cut off from the CPU proper. This makes it possible to reduce the amount of power consumed. Power is supplied to the display means when the cover 0 is opened, in which state power is delivered to the CPU every minute, namely at the time updating interval, to display and update the time. This improves the driving ratio of the CPU with respect to time to minimize the power consumed thereby.

Though the invention has been described with regard to an embodiment in which a battery serves as the power supply, the invention is not so limited. If the invention adopts a commercial AC power supply as the power supply, the amount of power consumed can be greatly reduced.

In the illustrated embodiment, power is supplied to the CPU in response to a pulse signal generated every minute. However, if the information relating to blood pressure measurement need only be obtained once per hour, an arrangement can be adopted in which the pulse signal is generated every hour. It is also possible to set the pulse generation period to any other value.

ADVANTAGES OF THE INVENTION

Thus, in accordance with the invention as described above, power consumption can be reduced by supplying power to peripheral circuits and peripheral devices when they are required during blood pressure measurement processing. When a battery is employed as the power supply, the life of the battery can be prolonged.

The invention makes it possible to cut off power to the CPU proper. Therefore, if an input is not obtained again from the switch commanding the start of blood pressure measurement or the start of printing processing after blood pressure measurement or the print-out of measured value ends, power is cut off to the CPU itself. This makes it possible to further reduce power consumption.

In the time display mode of operation, the time display is updated by supplying power to the related control circuitry such as the CPU only when the time is updated. This makes it possible to hold power consumption to the minimum.

As many apparently widely different embodiments of the present invention can be made without departing from the spirit and scope thereof, it is to be understood that the invention is not limited to the specific embodiments thereof except as defined in the appended claims.

What we claim is:

1. An electronic sphygmomanometer for measuring blood pressure of a patient, comprising:
    a power source;
    a cuff for wrapping around an arm of the patient;
    amplifying circuit means for supplying an analog signal corresponding to pressure inside said cuff;
    converting circuit means for converting the analog signal supplied by said amplifying circuit means into a digital signal;
    pump means for increasing air pressure inside said cuff;
    printer means for printing out the blood pressure information;
    connecting means for connecting said power source with said amplifying circuit means, said converting circuit means, said pump means and said printer means, selectively and independently; and
    processing means for controlling said electronic sphygmomanometer to perform the blood pressure measurement and for controlling said connecting means to connect said power source to said amplifying circuit means, said converting circuit means and said pump means while measuring blood pressure and to connect said power source to said printer means while printing measured blood pressure.

2. An electronic sphygmomanometer according to claim 1, wherein said power supplying means comprises a battery power supply incorporated in the electronic sphygmomanometer and operatively connected to said processing unit means.

3. An electronic sphygmomanometer according to claim 1, wherein said connecting means comprises a plurality of switches, each controlled by said processing means, for providing connection between said power source and said amplifying circuit means, said converting means, said pump means and said printer means, respectively.

4. An electronic sphygmomanometer according to claim 1, wherein said power supplying means comprises means for connecting said processing unit means to a commercial power supply external to the electronic sphygmomanometer.

5. An electronic sphygmomanometer according to claim 1, wherein said connecting means disconnects said power source from said pump means when pressure inside said cuff attains a predetermined pressure value.

6. An electronic sphygmomanometer according to claim 1, further comprising manual switches, connected to said power source, for initiating blood pressure measurement and printing and preventing connection of said power source to said amplifying circuit means, said converting means, said pump means and said printer means until said manual switches have been actuated.

7. An electronic sphygmomanometer comprising:
    timekeeping means, supplied with power at all times, for outputting a pulse signal of a predetermined duration at fixed intervals determined by a minimum time unit to be displayed and for holding time information;
    display means for displaying the time information and measured blood pressure information;
    cover means for covering at least said display means;
    first power supply means for supplying said display means with power to produce a display enable state in response to detecting that said cover means is open;

second power supply means for supplying power at least during the predetermined duration of the pulse signal output by said timekeeping means, when said display means is placed in the display enable state; and processing means for controlling blood pressure measurement performed by said electronic sphygmomanometer, said processing means including power receiving means for receiving power from said second power supply means to power said processing means;

first signal output means for outputting an inhibit signal to said second power supply means to inhibit any interruptions in the power supplied therefrom, when said pulse signal is output by said timekeeping means;

read-in means for reading in the time information from said timekeeping means after the inhibit signal is output by said first signal output means;

output means for outputting the time information, read in by said read-in means, to said display means; and second signal output means for outputting a signal to said second power supply means to permit interruptions after the time information is subsequently output by said output means.

8. An electronic sphygmomanometer according to claim 7, further comprising a memory for storing plural items of the blood pressure information whenever the blood pressure measurement is performed, said memory being supplied with power at all times to hold the items of the blood pressure information.

9. An electronic sphygmomanometer according to claim 7,
wherein said electronic sphygmomanometer further comprises an electronic sphygmomanometer body capable of enclosing, in cooperation with said cover means, said timekeeping means, said display mean, said first and second power supply means and said processing unit means, and wherein said cover means is a cap covering a portion of said electronic sphygmomanometer body.

10. An electronic sphygmomanometer according to claim 7, wherein the predetermined duration of the pulse signal output by said timekeeping means is at least as long as an amount of time between generation of a leading edge of the pulse signal and said processing means becoming operational.

11. An electronic sphygmomanometer according to claim 7, wherein said cover means is a case for accommodating said timekeeping means, said display means, said first and second power supply means and said processing means.

12. An electronic sphygmomanometer according to claim 7, wherein each of the fixed intervals of the pulse signal outputted by said timekeeping means in one minute.

* * * * *